United States Patent [19]

Lang et al.

[11] Patent Number: 4,923,977

[45] Date of Patent: May 8, 1990

[54] COSMETIC COMPOSITION BASED UPON N-HYDROXYPROPYLISOPROPYLETHER CHITOSANS AS WELL AS NEW N-HYDROXYPROPYLISOPROPYLETHER DERIVATIVES OF CHITOSAN

[75] Inventors: Günther Lang, Reinheim; Gerhard Maresch; Hans-Rudi Lenz, both of Darmstadt, all of Fed. Rep. of Germany

[73] Assignee: Wella Aktiengesellschaft, Darmstadt, Fed. Rep. of Germany

[21] Appl. No.: 228,928

[22] PCT Filed: Dec. 12, 1987

[86] PCT No.: PCT/EP87/00774

§ 371 Date: Jul. 29, 1988

§ 102(e) Date: Jul. 29, 1988

[87] PCT Pub. No.: WO88/05790

PCT Pub. Date: Aug. 11, 1988

[30] Foreign Application Priority Data

Feb. 7, 1987 [DE] Fed. Rep. of Germany ....... 3703760

[51] Int. Cl.$^5$ ..................... C08B 37/08; A61K 31/73; A61K 7/00; A61L 9/04
[52] U.S. Cl. ..................... 536/20; 514/55; 514/846; 514/881; 424/45; 424/47
[58] Field of Search .................. 536/20; 514/55, 846, 514/881; 424/45, 47

[56] References Cited

U.S. PATENT DOCUMENTS 4,528,283 7/1985 Lang et al. ..................... 536/20

FOREIGN PATENT DOCUMENTS 3223423 12/1983 Fed. Rep. of Germany ........ 536/20

*Primary Examiner*—Ronald W. Griffin
*Assistant Examiner*—Everett White
*Attorney, Agent, or Firm*—Michael J. Striker

[57] ABSTRACT

The present invention relates to a cosmetic for the treatment of hair and skin which is characterized by a content of novel N-hydroxy-propyl-isopropyl ether chitosans consisting of (a) 4 to 40 mole percent of monomer units having the formula (I)

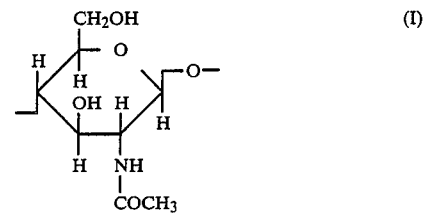

and (b) 60 to 96 mole percent of monomer units having the formula (II)

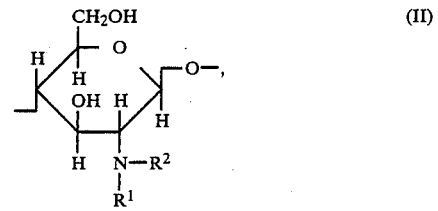

wherein $R^1$ and $R^2$ are identical or different and represent hydrogen or the group

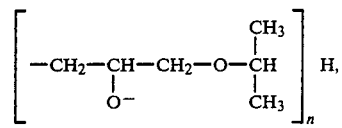

wherein n equals 1 or 2, with the condition that in at least half the units having the formula (II) $R^1$ and $R^2$ do not simultaneously represent hydrogen. The present invention also relates to novel N-hydroxy-propyl-isopropyl ether chitosans.

10 Claims, No Drawings

COSMETIC COMPOSITION BASED UPON N-HYDROXYPROPYLISOPROPYLETHER CHITOSANS AS WELL AS NEW N-HYDROXYPROPYLISOPROPYLETHER DERIVATIVES OF CHITOSAN

The present invention relates to a cosmetic composition for the treatment of hair or skin said composition containing a novel macromolecular compounds derived from chitosane. These compounds are used in the form of a suitable cosmetic base.

The present invention also relates to N-hydroxy-propyl-isopropyl ether chitosanes.

In cosmetic compositions, particularly for the treatment of hair, the use of cationic polymers, in particular polymers containing quaternary ammonium groups, as conditioners is known. Because of an interaction between their ammonium groups and the anionic groups of the hair the cation-active polymers have a great affinity for the keratin fibre.

It has been found that the use of this type of cationic-active polymer in these cosmetic agents has numerous advantages namely the disentanglement of the hair and, furthermore, springiness and a lustrous effect are imparted to the hair. However, because of the affinity for the keratin these polymers tend to build-up on the hair upon repeated application so that the hair becomes heavier which is undesirable for the final effect.

Furthermore, in synthetic polymers there are encountered problems due to the physiological effect of possibly present monomer traces which can be removed from the polymer only with difficulties.

Attempts have already been made to remove the above-mentioned disadvantages by applying to these cosmetics water-soluble salts of chitosan, a polyglucosamine that can be produced by deacetylation of chitin. In this connection reference is made to the applicant's EP-PS No. 0 002 506 and DE-PS No. 26 27 419.

In the same manner as in the majority of the cation-active polymers with quaternary grouping chitosan frequently also has the disadvantage that it is only slightly compatible with the anion-active surface-active agents conventionally used for the treatment of hair, particularly in shampoos. Therefore, it is necessary to allow the chitosan to have an effect in separate treatments, namely prior to and/or after the application of the shampoo. Furthermore, it has been found that chitosan is practically insoluble in a neutral and alkaline medium so that, for example, its application in alkaline permanent wave agents or hair dyes is not possible.

By applying glycidyl chitosans according to the applicant's DE-OS No. 32 23 423 instead of chitosan salts the above-mentioned disadvantages can actually be avoided but the reaction of chitosane with glycide presents a problem since glycide rapidly hydrolyzes in the presence of water.

The above-mentioned chitosans and chitosan derivatives have a further disadvantage, namely, in organic solvents they are not or only slightly soluble so that the possibilities of applying them in cosmetics are substantially restricted.

Therefore, the present invention provides anion surfactant-compatible chitosan derivatives which are suitable for the application in both aqueous cosmetics and anhydrous cosmetics.

On continuing the tests with chitosan and the compounds derived therefrom it has now been found that specific chitosan derivatives, i.e., particularly N-hydroxy-propyl-isopropyl ether chitosans, have a good compatibility with anion surfactants. These derivatives are soluble in organic solvents, as for example, ethanol and isopropanol, and thus allow the production of anhydrous, for example, alcoholic solutions.

Unlike synthetic polymers having finite residual monomer contents these N-hydroxy-propyl-isopropyl ether chitosans are physiologically harmless and biologically degradable. Because of their film properties, their alcohol-solubility and their thickener effect as well as their anion surfactant compatibility not only can they be applied as novel interesting raw materials for cosmetic compositions, but they can also be used in pharmacy, as flocculants and thickners in sewage treatment, as finishing agents and sizing agents in the textile industry and in paper making.

With N-hydroxy-propyl-isopropyl ether chitosan there can thus be produced a cosmetic composition for the treatment of hair and skin which is distinguished by surprisingly favorable properties and is characterized in that it contains in a suitable cosmetic base an N-hydroxy-propyl-isopropyl ether chitosan consisting of (a) 4 to 40 mole percent of monomer units having the formula (I)

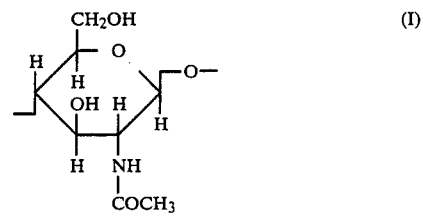

and (b) 60 to 96 mole percent of monomer units having the formula (II)

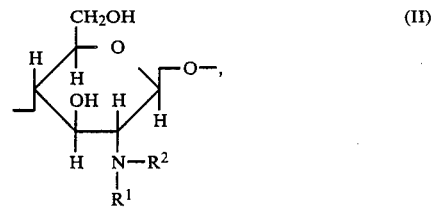

wherein $R^1$ and $R^2$ are identical or different and represent hydrogen or the group

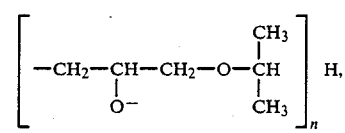

wherein n equals 1 or 2, on the condition that in at least half the units having the formula (II) $R^1$ and $R^2$ do not simultaneously represent hydrogen.

The agent containing N-hydroxy-propyl-isopropyl ether chitosane is quite generally suitable for the treatment of hair and skin. It can be used in the form of a shampoo and/or body care agent into shampoo, hair dressing cream, hair dressing lotion, hair drying lotion, washing lotion, hair curative, agent for fixing the hairdo, agent for the permanent shaping of hair, agent for treating dandruff, agent for dyeing hair or removing the dye therefrom, as an agent for application prior to and after dyeing the hair and as a cosmetic for the care, protection and cleaning of the skin. Examples of this type of agent for the care and cleansing of the skin are face lotions, shaving lotions, cold creams, body lotions, sunscreen agents as well as make-up preparations.

In this case the content of N-hydroxy-propyl-isopropyl ether-chitosan in the cosmetic composition according to the present invention suitably is 0.05 to 10 percent by weight, preferably 0.05 to 3.0 percent by weight.

The cosmetic composition according to the present invention can contain, for the production of a cosmetic base, all the components which are conventionally used in the agents for treating hair and skin, particularly anionic, cationic, amphoteric, zwitter-ionic or non-ionic surface active compounds (surfactants), foam synergists, stabilizers, sequestering agents, pigments, thickeners, emulsifiers, buffer substances, preservatives, dyes, perfume oils, known cosmetic polymers such as anionic, non-ionic, cationic or amphoteric polymers, natural substances, cosmetic oils, fatty alcohols, waxes, froth stabilizing agents, active ingredients against dandruff, reducing agents and propellants in addition to the novel active substance N-hydroxy-propyl-isopropyl ether chitosan.

The cosmetic composition according to the present invention preferably has a pH value of 2 to 12 and can be present in the form of an aqueous, alcoholic or aqueous-alcoholic preparation, particularly as a solution, cream, gel, dispersion or emulsion.

It is also possible to take this agent from a pressure vessel with the aid of an atomizer or any other suitable spraying device or in admixture with conventional propellants liquefied under pressure as aerosol spray (for example, aerosol hair spray) or aerosol foam.

The cosmetic composition according to the present invention preferably is an agent for fixing the hairdo, as for example, a liquid hair fixative or hair spray. This cosmetic composition usually is in the form of an aqueous, alcoholic or aqueous-alcoholic solution which is characterized by a content of N-hydroxy-propyl-isopropyl ether chitosan consisting of units having the above-mentioned formulae (I) and (II). In this case the N-hydroxy-propyl-isopropyl ether chitosane itself can be applied as a film-forming or stabilizing resin. However, other film-forming natural or synthetic cosmetic polymers can also be contained in the hair fixative according to the present invention. For example, shellac, alginates, gelatin, pectines and cellulose derivatives are suitably as natural polymers. For example, the following synthetic polymers are used: polyvinyl pyrrolidone, polyvinyl acetate, polyacrylic compounds, as for example, acrylic acid, methacrylic polymers, basic polymers of esters from acrylic acid or methacrylic acid with aminoalcohols or the salts or quaternization products of these basic polymers, polyacrylonitrile as well as copolymers or terpolymers of these compounds, for example, polyvinyl pyrrolidone-vinyl acetate.

In this case the cosmetic composition has a pH value particularly of between 6 and 8. This agent for fixing the hairdo conventionally contains the film-forming polymers in a total amount of approximately 0.05 to 3.0 percent by weight. When the cosmetic composition also contains other film-forming polymers in addition to the above-described N-hydroxy-propyl-isopropyl ether chitosan consisting of units having the formulae (I) and (II), then the content of hydroxy-propyl-isopropyl ether chitosan decreases correspondingly.

Suitable alcohols are particularly the lower alcohols containing 1 to 4 carbon atoms which are conventionally used for cosmetic purposes, as for example, ethanol and isopropanol.

When the agent for fixing the hairdo is in the form of an aerosol preparation, which is sprayed from a pressure vessel, then it contains approximately 10 to 60 percent by weight of a propellant in the cosmetic base. Suitable propellants are chloro-fluoro alkanes, as for example, $CCl_3F$, $CCl_2F_2$, $C_2Cl_3F_3$, $(CCl_2F)_2$, $CHCl_2F$ and $(CClF_2)_2$, readily volatile hydrocarbons, as for example, n-butane and n-propane, or even dimethyl ether, carbon dioxide, dinitrogen monoxide, nitrogen, methylene chloride and 1,1,1-trichloroethane.

The agent according to the present invention for fixing the hairdo can also contain the conventional additives used for these agents, as for example, perfume oils, bactericides or fungicides, substances improving the combability, as for example, silicone oil, or softening agents, as for example, isopropyl myristate, phthalic diethyl ester and diethyl stearate.

When required, the agent according to the present invention for fixing the hairdo can simultaneously dye or tint the hair with a content of cosmetic dyes. These preparations are also known commercially as dye or tinting strengtheners. They additionally contain conventional direct cosmetic dyes used for hair fixatives (for example, 1,4-diamino-2-nitro benzene, picramic acid, 1-hydroxy-2-amino-4-nitro-benzene and 1,4-bis-[(2-hydroxy-ethyl)-amino]-2-nitro-5-chloro benzene), azo dyes (for example, C.I. 14 805-Acid Brown 4), anthraquinone dyes (for example, C.I. 61 105-Disperse Violet 4) and triphenyl-methane dyes (for example, C.I. 42 535-Basic Violet 1). Depending on the type of their substituents the dyes of these classes can have an acid, non-logenic or basic character. Their total concentration in these preparations commonly is approximately 0.01 to 2.0 by weight.

As compared with conventional hair fixatives the agent according to the present invention has, at equally good fixation of the hair, a particularly good combability and a good feel of the hair in the wet state and a particularly good feel of the hair in the dry state.

Furthermore, the agent according to the present invention can also be a shampoo. In this case it is in the form of an aqueous solution or emulsion and contains at least one anionic, cationic, non-ionic or amphoteric surfactant in addition to the N-hydroxy-propyl-isopropyl ether chitosan.

In this shampoo the concentration of the surfactant generally is approximately 3 to 50 percent by weight, preferably 3 to 20 percent by weight while the pH value generally is between 3 and 9, preferably between 4 and 7.

The agent according to the present invention, which is in the form of a shampoo generally contains various additives, particularly perfumes, preservatives, thickeners, foam stabilizing agents, buffer substances, cosmetic resins, pigments and dyes.

Among the foam stabilizing agents the fatty amides and particularly the mono-or diethanol amides of coconut fatty acids, lauryl-or oleic acid mono-or diethanol amide are mentioned here; they are suitably applied in amounts of 1 to 10, preferably 1 to 3 percent by weight. Among the thickeners particularly the acrylic polymers and cellulose derivatives, as for example, carboxymethyl cellulose, hydroxy-propyl methyl cellulose, and hydroxy-ethyl cellulose, are cited. In general, the thickeners are present in amounts of 0.1 to 5 percent by weight.

Among the surfactants or surface-active agents which are used in combination with the novel N-hydroxy-propyl-isopropyl ether chitosans, for example, the following agents are mentioned: (a) the anionic surface-active agents, as for example, the alkali, alkaline earth, ammonium or alkanol salts of alkane sulphonates, alkyl sulphates and alkyl ether sulphates, the $C_{12}$ to $C_{18}$-alkyl and particularly $C_{12}$ to $C_{14}$-alkyl sulphate sodium salts or triethanol amine salts, the sodium or triethanolamine salts of lauryl or tetradecyl ether sulphates, the disodium salt of sulphosuccinic semi-ester of alkanol amides, the soaps and the polyether carboxylic acids; (b) the non-ionic surface-active agents, as for example, oxyethylated fatty alcohols containing 12 to 18 carbon atoms, with, for example, up to 40 moles of ethylene oxide per mole of fatty alcohol, oxyethylated lauryl, tetradecyl, cetyl, oleyl and stearyl alcohol, alone or in mixture; the fatty alcohols of oxyethylated lanolin, or oxyethylated lanolin; polyglycol ether of saturated or unsaturated fatty alcohols and alkyl phenols containing 8 to 30 carbon atoms in the alkyl radical and 1 to 10 glyceryl units in the molecule; fatty acid alkanol amides and oxyethylated sorbitan fatty ester; (c) the cationic surface-active agents, as for example, the dilauryl dimethyl ammonium chloride, the chlorides or bromides of alkyl dimethyl benzyl ammonium, the alkyl trimethyl ammonium salts, for example, cetyl trimethyl ammonium chloride or bromide, the alkyl dimethyl hydroxyethyl ammonium chlorides or bromides, the dialkyl dimethyl ammonium chlorides or bromides, alkyl pyridinium salts for example, lauryl or cetyl pyridinium chloride, the alkyl amide ethyl trimethyl ammonium ether sulphates, compounds having a cationic character, such as amine oxides, for example, alkyl dimethyl amineoxides or alkyl amino-ethyl dimethyl amine oxides; (d) the amphoteric or zwitter-ionic surface-active agents, for example, the carboxyl derivatives of imidazole, the N-alkyl betaines, the N-alkyl-amido betaines, the N-alkyl sulphobetaines, the N-alkyl-amino-proprionates, the alkyl dimethyl ammonium acetates, the $C_{12}$ to $C_{18}$-alkyl dimethyl carboxy methyl ammonium salts as well as the fatty acid alkyl amidobetaines, for example, dimethyl-carboxy methylene propylene amido stearate betaine.

The cosmetic compositions according to the present invention can also be a cream or lotion for use as a hair curative or as a skin care aid. In this case it is mostly in the form of an oil-in-water or water-in-oil emulsion or suspension and, additionally to the novel N-hydroxy-propyl-isopropyl ether chitosans, it contains cationic, non-lonogenic, amphoteric or anionic emulsifiers and, as a component of the oil phase, for example, fatty alcohols, fatty esters or amides, as well as perfume oils, petrolatum, wool fatty alcohol or solid and liquid paraffins.

When the cosmetic composition according to the present invention is a hair tinting agent or a hair dye, then it also is preferably in the form of a cream or lotion and additionally contains conventional hair dyes from the group of the aromatic nitro dyes, azo dyes, anthraquinone dyes, triphenyl-methane dyes or even oxidation dyes, for example, resorcinol and aromatic diamines or aminophenols. Furthermore, when required, this cosmetic composition contain alkalizing agents, antioxidants as well as cosmetic additives and auxiliary substances used for this kind of cosmetic.

The cosmetic composition according to the present invention can also be a permanent wave agent or a fixative for hair. In this case it contains, additionally to said N-hydroxy-propyl-isopropyl ether chitosans, a reducing agent, as for example, thioglycolic acid, thiolactic acid and ammonium sulphite, or an oxidizing agent, as for example, hydrogen peroxide or sodium bromate, and, when required, alkalizing agents or peroxide stabilizers, for example, phosphoric acid, and other cosmetic auxiliary substances and additives, as for example, perfume oils, perfumes, care agents and dyes.

As mentioned hereinbefore, the cosmetic according to the present invention can also be used for the treatment of the skin.

In fact this cosmetic composition promotes the moistening of the skin, prevents drying and imparts to the skin the feel of an excellent softness.

For this purpose the cosmetic according to the present invention is preferably in the form of a cream, a gel, an emulsion or of an aqueous, alcoholic or aqueous-alcoholic solution which contains the N-hydroxy-propyl-isopropyl ether chitosans in a concentration of 0.1 to 10 percent by weight, preferably 0.2 to 6 percent by weight.

The auxiliary substances generally contained in this kind of cosmetic preparation are, for example, perfumes, dyes, preservatives, thickeners, sequestering agents, emulsifiers, sun protection filters and the like.

This preparation for treating the skin is particularly in the form of a cream or lotion for the care of the hands and the face or in the form of a sunscreen cream, a colored cream, a cream for removing makeup, a foam bath or shower-bath preparation or even in the form of a deodorant preparation.

This preparation is produced by means of classical processes. For example, for the production of a cream an aqueous phase, which contains the chitosan derivative according to the present invention and, when required, other ingredients or auxiliary substances in the dissolved form, and an oily phase can be emulsified. For the oily phase various compounds can be used, for example, paraffin oil, vaseline oil, sweet almond oil, avocado oil, olive oil, fatty acid ester, as for example glyceryl monostearate, ethyl palmitate and isopropyl palmitate or alkyl myristate, as for example, propyl myristate, butyl myristate and cetyl myristate. They can also be mixed with fatty acid alcohols, for example, stearyl or cetyl alcohol, or waxes, for example beeswax or wool wax.

The N-hydroxy-propyl-isopropyl ether chitosans can be contained in this cosmetic preparation for the care of the skin both as principal active ingredient and auxiliary substance.

The novel N-hydroxy-propyl-isopropyl ether chitosans contained in the cosmetic according to the present invention are derived from chitosan, a material obtained by deacetylation of chitin, which is a naturally occurring acetyl glucosamine.

The chitosan is insoluble in a neutral and alkaline medium, but because of its chemical nature it forms soluble salts with specific organic and inorganic acids in an acid medium. These soluble salts are used as additives in the paper and textile industries. Furthermore, they are used as coagulants for suspensions, as chelating agents for heavy metal ions as well as in medical science and in the cosmetics industry (in this connection see the publication by Muzaieill: "Chitin", Pergamon Press, 1977).

A number of water-soluble chitosan derivatives are already known (for example, carboxy-methyl chitosane (see Nud'ga, Plisko and Danilov, Zhur. Obsh. Khim. 43, No. 12, page 2752 to 2756 (1973); SU-PS No. 325 234, as well as Okimasu, Nippon, Nogel, Kagaku Kaishi 32, No. 5, page 383 to 389 and 471 to 473 (1958) or sulphoethyl chitosan (see Nud'ga, Plisko and Danilov, Zhur Prikl. Khim. 47 No. 4, Page 872 to 875 (1974)). However, these water-soluble chitosan derivatives either have been changed in their ionic character or they are physiologically harmful.

Hydroxy-ethyl chitosan (glycol chitosan) was obtained by Senju and Okimasu (Nippon Nogel Kagaku Kaishi 23, Page 432 to 437 (1950)) by glycolation of chitin in the presence of strong alkali by simultaneous deacetylation.

Because of low degrees of substitution, and cross-linking water-insoluble hydroxy alkyl derivatives of chitosan, whose intensely water-absorbing properties are of interest in the application technology, are mentioned in JP-PS No. 54-11 955 of 1979.

Finally, JP-PS No. 57-180 602 (1982) describes the synthesis of water-soluble chitosan derivatives obtained by reaction of alkylene oxides with chitosan in the presence of alkali in a mixture of water and an organic solvent.

All these more or less water-soluble or water-swellable derivatives are based on the reaction of the chitosan with alkylating agents in the presence of strong alkalis. Under the reaction conditions selected this reaction results exclusively or preponderantly in an O substitution. However, not only does the presence of alkali, which is required for the O alkylation, determine the place of substitution, but there beyond it causes a degradation of the polymer chain, particularly at elevated temperatures. Furthermore, the salts forming after the reaction by neutralization of the excess alkali are by-products which require further purification steps.

In contrast thereto, the applicant's DE-OS No. 32 23 423 and the applicant's EP-OS No. 0 097 229 relate to water-soluble N-substituted chitosan derivatives which are preferably obtained by the reaction of an aqueous dispersion of chitosan with glycide. However, the rapid hydrolysis of the glycide in the presence of water, its high price and the fact that glycide cannot be produced on a large industrial scale renders the process for producing these derivatives more expensive.

It has now been found that on using mixtures of water and organic solvents chitosan can be converted in a simple manner with 2,3-epoxy-propyl-isopropyl ether to N-hydroxy-propyl-isopropyl ether derivatives having particularly favorable film and solubility properties. Unlike the N-dihydroxy-propyl chitosans known from the applicant's DE-OS No. 32 23 423 these novel hydroxy-propyl-isopropyl ether derivatives of chitosan are soluble in water and in diluted acids as well as in alcohols and, therefore, they are also suitable for the use in anhydrous, particularly alcoholic agents.

In the absence of basic catalysts there thus results the substitution of the free amino groups. This is confirmed by the determination of the primary amine nitrogen according to van Slyke (see K. H. Bauer and H. Moll, "Die organische Analyse" 2nd Edition, Page 170 to 172, Akademische Veriagsgesellschaft Geest und PortigkG, Leipzig 1950, and H. Roth, E. V. Hulle et al. in "Analytische Methoden", Page 674 to 676, Georg thieme Verlag, Stuttgart 1953) and by $^{13}$C-NMR.

Therefore, the present invention relates to water-soluble and alcohol-soluble N-hydroxy-propyl-isopropyl-ether compounds derived from chitosan and consisting of (a) 4 to 40 mole percent of monomer units having the formula (I)

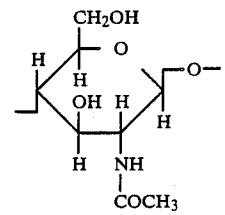

and (b) 60 to 96 molar percent of monomer units having the formula (II)

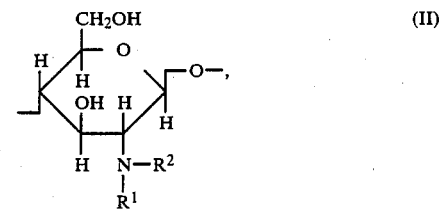

wherein $R^1$ and $R^2$ can be identical or different and represent either hydrogen or the group

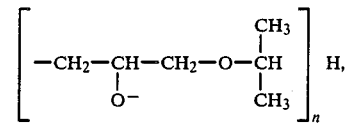

wherein n equals 1 or 2, on the condition that in at least half the units having the formula (II) $R^1$ and $R^2$ do not simultaneously represent hydrogen, or their water-soluble salts.

Analogously to the first stage of the two-stage process for producing O-alkyl-N-hydroxy-propyl chitosans described in the applicant's DE-OS No. 35 04 095 the novel chitosan derivatives are obtained in that a suspension of chitosan (60 to 96 percent of deacetylated chitin) or its salts are reacted at temperatures of between 20° and 120° C., preferably between 40° and 100° C., under pressure in an autoclave with 2,3-epoxy-propyl-isopropyl ether in a suitable ratio over a period of 3 to 72 hours preferably 6 to 48 hours.

In a preferred method the reaction is carried out in a mixture consisting of water and an organic solvent in a neutral medium. When using chitosan salts or chitosan in the presence of acid catalysts, as for example, hydrochloric acid, the reaction can be carried out in a dispersion or solution consisting of water and an organic solvent or water and excess 2,3-epoxy-propyl-isopropyl ether. The molar ratio of chitosan to epoxide is between 1:3 and 1:15.

When the reaction is completed the excess alkylating agent is removed, possibly present insoluble components are separated from the solutions of the chitosan derivative by filtration, followed, when required by neutralization. The solutions are then concentrated in a rotation evaporator and the chitosan derivatives are precipitated either directly or after the dialysis in acetone.

By neutralization of the amino groups with inorganic or organic acids the N-hydroxy-propyl-isopropyl ether chitosan according to the present invention can be converted into the corresponding salts. However, according to the present invention only salts that are soluble in water can be used. Suitable salts are, for example, those that are formed with hydrochloric acid, glycolic acid, lactic acid, formic acid, citric acid or acetic acid.

The present invention will be explained in greater detail by the examples hereafter without restricting it then.

EXAMPLES OF PRODUCTION

EXAMPLE 1

50 g (0.31 mole) of low-molecular ground chitosan having a limiting viscosity number (Eta) of 160 ml per gram and a degree of deacetylation of 90 percent are dispersed in 400 ml of isopropanol/water (1:1) and mixed with 144 g (156.6 ml=1,24 moles) of 2,3-epoxy-propyl-isopropyl ether in an autoclave while stirring. After a reaction time of 12 hours at 100° C. the reaction product is concentrated to dryness with the aid of a rotation evaporator and then dried at 50° C. in a vacuum shelf dryer. The residue is subsequently dissolved in 1000 ml of ethanol. Upon pressure filtration for the removal of non-reacted components the filtrate is concentrated in vacuo to 300 ml and is precipitated in 8 to 10 times the amount of acetone with the aid of a stirrer.

The precipitate is collected on a glass sinter suction filter, thoroughly washed with acetone and dried in vacuo at 50° C.

48 g of N-hydroxy-propyl-isopropyl ether chitosan are obtained.

Characteristic Data

| limiting viscosity number (Eta) | = | 60 ml/g |
|---|---|---|
| degree of substitution hydroxy-propyl-isopropyl ether | = | 0.9 |
| pendulum hardness | = | 174 seconds |
| steam absorption | = | 4.8 percent. |

EXAMPLE 2

20 g (0.12 mole) of a high-molecular chitosan having a limiting viscosity number (Eta) of 1600 ml per gram and a deacetylation degree of 76 percent are dispersed in a pressure vessel in 600 ml of ethylene glycol dimethyl ether/water (8:2), mixed with 111.5 g (121.2 ml=0.96 mole) of 2,3-epoxy-propyl-isopropyl ether and reacted for 20 hours at 80° C. while stirring. The further processing is like that described in Example 1.

The yield of N-hydroxy-propyl isopropyl ether chitosan is 26.2 g.

| Limiting viscosity number (Eta) | = | 194 ml/g |
|---|---|---|
| Degree of substitution hydroxy-propyl-isopropyl ether | = | 1.3 |
| pendulum hardness | = | 170 seconds |
| steam absorption | = | 5.2 percent. |

EXAMPLE 3

50 g (0.31 mole) of low-molecular ground chitosan having a limiting viscosity number (Eta) of 160 ml per gram and a deacetylation degree of 90 percent are dispersed in 200 ml of isopropanol/water (1:1) while adding 43.8 g (0.3 mole) of a 25 percent hydrochloric acid and are reacted in an autoclave with 209.1 g (227.3 ml=1.8 moles) of 2,3-epoxy-propyl-isopropyl ether for 24 hours at 90° C. The reaction product is further processed after neutralization and dialysis as described in Example 1.

44 g of N-hydroxy-propyl-isopropyl ether chitosan are obtained.

Characteristic Data

| limiting viscosity number (Eta) | = | 35 ml/g |
|---|---|---|
| degree of substitution hydroxy-propyl-isoproyl ether | = | 1.7 |
| pendulum hardness | = | 161 seconds |
| steam absorption | = | 7.3 percent. |

The degree of substitution for the hydroxy-propyl-isopropyl ether radicals was determined with the aid of the $^1$H-NMR spectra.

The measurements of the limiting viscosity numbers was carried out in an aqueous solution of 0.2 mole/liter of acetic acid and 0.1 mole/liter of sodium acetate (chitosan) and in an aqueous solution of 0.2 mole/liter of acetic acid and 0.1 mole/liter of sodium chloride (N-hydroxy-propyl-isopropyl-ether chitosan) at 25° C., using a DIN Ubbelohde capiliary viscometer.

The pendulum hardness was determined according to W. König, "Härtemessungen mit dem Pendelhärteprüfer", Farbe und Lack 65, Page 435 to 443 (1959); DIN 53 157).

The steam absorption was determined at a relative humidity of 70 percent as compared with a relative humidity of 30 percent.

EXAMPLES OF COSMETICS

EXAMPLE 4

Hairspray (free from propellent)

2.5 g of N-hydroxy-propyl-isopropyl ether chitosan according to Example 3 (Eta=35 ml per gram, degree of substitution=1.7)

| 61.5 g ethanol |
| 35.5 g of isopropanol |
| 0.5 g of perfume oil |
| 100.0 g |

EXAMPLE 5

Hair Fixative 0.6 g of N-hydroxy-propyl-isopropyl ether chitosan according to Example 1 (Eta=60 ml per gram, degree of substitution=0.9).

| 25.0 g of isopropanol |
| 0.4 g of formic acid (10 percent aqueous solution) |
| 0.2 g of perfume oil |
| 73.8 g of water |
| 100.0 g. |

20 ml of this solution are distributed on the washed and towel-dried hair, whereupon the hair is laid for the desired hairdo in the usual manner and dried. As compared with a hair fixative based on chitosan/formic acid the hair has a more pleasant and softer feel while the fixation effect is good.

EXAMPLE 6

Spray Blow-Drying Lotion

| | |
|---|---|
| 0.5 g | of N-hydroxy-propyl-isopropyl ether chitosan according to Example 3 (Eta = 3.5 ml per gram), degree of substitution = 1.7). |
| 58.0 g | of isopropanol |
| 0.4 g | of phthalic diethyl ester |
| 0.4 g | of perfume oil |
| 0.1 g | of cetyl trimethyl ammonium chloride |
| 40.6 g | of water |
| 100.0 g. | |
| Filling proportion: | 91 percent of active ingredient |
| | 9 percent of propane/butane (pressure: 0.27 MPa at 20° C.). |

The blow-dry lotion is sprayed on the washed and towel-dried hair, whereupon the hair is blow-dried and shaped in the usual manner. Compared with a blow-dry lotion with synthetic polymers and with good conditioning the hair has a much more pleasant and softer feel.

EXAMPLE 7

Tinting strengthener

| | |
|---|---|
| 0.60 g | N-hydroxy-propyl-isopropyl ether chitosan according to Example 1 (Eta = 60 ml per gram, degree of substitution = 0.9) |
| 45.00 g | of ethanol |
| 0.15 g | of 1,4-bis-[(2-hydroxy-ethyl)-amino]-2 nitro -5-chloro benzene |
| 54.25 g | of water |
| 100.0 g | |

20 ml of this solution are applied to the washed and towel-dried hair, whereupon the hair is laid and dried. The hair has been dyed violet and fixed.

EXAMPLE 8

Anionic Shampoo

| | |
|---|---|
| 1.00 g | of N-hydroxy-propyl-isopropyl ether chitosan according to Example 2 (Eta = 194 ml per gram, degree of substitution = 1.3) |
| 40.00 g | of lauryl alcohol diglycol ether sulphate sodium salt (28 percent aqueous solution) |
| 4.00 g | of sodium chloride |
| 0.10 g | of formaldehyde (25 percent acqueous solution) |
| 0.05 g | of dye |
| 54.85 g | of water |
| 100.00 g. | |

A clear shampoo is obtained. With regard to feel, gloss and combability the hair washed therewith has been excellently conditioned.

EXAMPLE 9

Amphoteric Tinting Shampoo

| | |
|---|---|
| 2.00 g | of N-hydroxy-propyl-isopropyl ether chitosan according to Example 1 (Eta = 60 ml per gram, degree of substitution = 0.9) |
| 40.00 g | of dimethyl-carboxy-methylene-propylene-amido-stearate betaine (35 percent aqueous solution) |
| 5.06 g | of formic acid (10 percent aqueous solution) |
| 3.50 g | of coconut oil acid (one percent aqueous solution |
| 1.00 g | picramic acid (one percent aqueous solution) |
| 48.44 g | of water, fully desalted |
| 100.00 g. | |

With 15 to 20 g of the above shampoo the hair is shampooed. After a reaction time of 5 to 10 minutes the hair is rinsed with water. The hair has a yellow-orange shade and is excellently conditioned.

EXAMPLE 10

Cationic Hair Curative

| | |
|---|---|
| 0.30 g | of N-hydroxy-propyl-isopropyl ether chitosan according to Example 2 (Eta = 194 ml per gram, degree of substitution is 1.3) |
| 4.00 g | of cetyl stearyl alcohol |
| 2.50 g | of coco(pentaethoxy)methyl ammonium chloride |
| 1.48 g | of lactic acid (10 percent aqueous solution) |
| 1.00 g | of sorbitan monopalmitate oxethylated with 20 moles of ethylene oxide |
| 90.72 g | of water, fully desalted |
| 100.0 g. | |

35 g of the hair curative according to Example 10 are spread in the washed hair and after a reaction time of 3 to 5 minutes the curative is rinsed out again with water. As a result an excellent feel, gloss and combability of the hair are obtained.

EXAMPLE 11

Hair Curative in the Form of a Gel

| | |
|---|---|
| 2.1 g | of N-hydroxy-propyl-isopropyl ether chitosan according to Example 2 (Eta = 194 ml per gram, degree of substitution = 1.3) |
| 0.6 g | of hydroxy-propyl methyl cellulose |
| 0.5 g | of lauryl pyridinium chloride |
| 96.8 g | of water, fully desalted |
| 100.0 g | (adjusted with a ten percent formic acid to pH 5.0). |

The application of the gel is carried out as described in Example 9. As a result the feel, gloss and combability of the hair are substantially improved.

EXAMPLE 12

Hair Tinting Agent

| | |
|---|---|
| 0.30 g | of N-hydroxy-propyl-isopropyl ether chitosan according to Example 1 (Eta = 60 ml per gram, degree of substitution = 0.9) |
| 12.00 g | of cetyl stearyl alcohol |
| 6.00 g | of lauryl alcohol diglycol ether sulphate sodium salt (28 percent aqueous solution) |
| 0.85 g | of 1,4-diamino-2-nitro-benzene |
| 0.50 g | of perfume oil |
| 0.50 g | of 1-hydroxy-2-amino-4-nitro-benzene |
| 0.24 g | of sodium hydroxide |
| 0.10 g | of 4-hydroxy-benzoic ethyl ester |
| 79.51 g | of water |
| 100.00 g. | |

30 to 40 g of the above hair tinting agent are spread in the washed hair and washed out after a reaction time of approximately 20 minutes. The hair has been dyed reddish and has a good combability and pleasant feel.

EXAMPLE 13

Oxidation Dye

| | |
|---|---|
| 0.50 g | of N-hydroxy-propyl-isopropyl ether chitosan according to Example 2 (Eta = 194 ml per gram, degree of substitution = 1.3) |
| 15.00 g | of cetyl alcohol |
| 3.50 g | of lauryl alcohol diglycol ether sulphate sodium salt (28 percent aqueous solution) |
| 3.00 g | of ammonium (25 percent, aqueous solution) |
| 0.30 g | of 1,4-diamino-benzene |
| 0.30 g | of sodium sulphate |
| 0.25 g | of resorcinol |
| 0.08 g | of 3.5 - diamino-2,6-diomethoxy-pyridine dihydrochloride |
| 77.07 g | of water |
| 100.00 g. | |

50 g of this hair dye are mixed with 50 ml of a 6 percent hydrogen peroxide solution and applied to white hair. After 30 minutes the hair is rinsed with water and dried. The hair then has a dull blond coloration of natural appearance and a natural pleasant feel.

EXAMPLE 14

Permanent Wave Agent

| | |
|---|---|
| 0.50 g | of N-hydroxy-propyl-isopropyl chitosan according to Example 3 (Eta = 35 ml per gram, degree of substitution = 1.7) |
| 10.0 g | of thioglycolic acid |
| 8.0 g | of ammonia (25 percent aqueous solution) |
| 6.1 g | of ammonium hydrogen carbonate |
| 75.4 g | of water |
| 100.0 g. | |

For its application this hair waving agent is evenly applied to the towel-dried hair (which is in rollers) and is allowed to react for approximately 20 minutes. The hair is then rinsed with water and oxidatively treated in a conventional manner. The hair has a natural and soft feel.

EXAMPLE 15

Skin Cream

| | |
|---|---|
| 0.30 g | of N-hydroxy-propyl-isopropyl ether chitosan according to Example 1 (Eta = 60 ml per gram, degree of substitution = 0.9) |
| 3.00 g | of stearyl alcohol |
| 1.00 g | of wool wax (Adeps Lanae) |
| 1.00 g | of petrolatum |
| 1.00 g | of sodium acetyl stearyl sulphate |
| 0.76 g | of lactic acid (10 percent aqueous solution) |
| 92.94 g | of water, fully desalted |
| 100.00 g. | |

Unless otherwise stated all the data in percent in the present application relate to percent by weight.

What is claimed is:

1. A cosmetic composition for the treatment of hair and skin which contains in a suitable cosmetic base an N-hydroxy-propyl-isopropyl ether chitosan consisting of (a) 4 to 40 mole percent of monomer units having the formula (I)

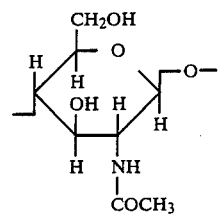

and (b) 60 to 96 mole percent of monomer units having the formula (II)

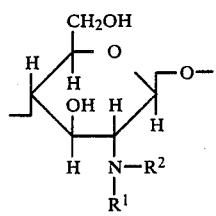

wherein $R^1$ and $R^2$ are identical or different and are hydrogen or the group

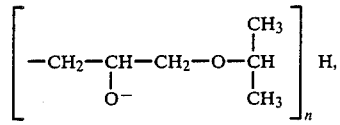

wherein n equals 1 or 2, with the condition that in at least half the units having the formula (II) $R^1$ and $R^2$ do not simultaneously represent hydrogen.

2. A cosmetic composition as in claim 1, which contains the N-hydroxy-propyl-isopropyl ether chitosan in an amount of 0.05 to 10 percent by weight.

3. A cosmetic composition as in claim 1 or 2, in the form of an aqueous, alcoholic or aqueous-alcoholic preparation, especially in the form of a solution, cream, gel, dispersion or emulsion.

4. A cosmetic composition as in claim 3, having a pH value from 2 to 12.

5. A cosmetic composition as in claim 4, which contains a film-forming synthetic or natural cosmetic polymer.

6. A cosmetic composition as in claim 5, which contains at least one cosmetic dye in a concentration of 0.01 to 2.0 percent by weight and is in the form of a dye strengthener or tinting strengthener.

7. A cosmetic composition as in claim 6, which contains as a cosmetic base an aqueous, alcoholic or aqueous-alcoholic preparation, which is mixed with a propellant liquifying under pressure, drawn off into a pressure vessel and is present in the form of an aerosol spray or foam.

8. A cosmetic composition as in claim 4, which contains at least one cationic non-ionic, amphoteric or anionic surfactant and is in the form of a shampoo.

9. A cosmetic composition as in claim 8, which contains the surfactant in a concentration of 3 to 50 percent by weight and has a pH value of between 3 and 9.

10. A macromolecular N-hydroxy-propyl-isopropyl ether compound derived from chitosan and consisting of (a) 4 to 40 mole percent of monomer units having the formula (I)

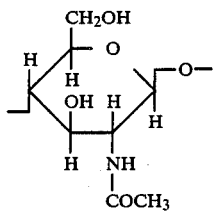
(I)
and (b) 60 to 96 mole percent of monomer units having the formula (II)
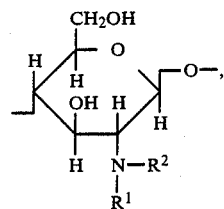
(II)
wherein $R^1$ and $R^2$ are identical or different and represent either hydrogen or the group
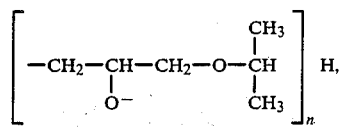
wherein n equals 1 or 2, with the condition that in at least half the units having the formula (II) $R^1$ and $R^2$ do not simultaneously represent hydrogen, or its water-soluble salt.
* * * * *